United States Patent [19]

Kurland

[11] 4,216,671

[45] Aug. 12, 1980

[54] AUTOMATIC CLEANING OF SENSING PROBES

[75] Inventor: Jerome J. Kurland, Chicago, Ill.

[73] Assignee: Metropolitan Sanitary District of Greater Chicago, Chicago, Ill.

[21] Appl. No.: 639,657

[22] Filed: Dec. 11, 1975

Related U.S. Application Data

[63] Continuation of Ser. No. 479,351, Jun. 14, 1974, abandoned.

[51] Int. Cl.² .................. B08B 7/02; B08B 7/04; G01N 33/18
[52] U.S. Cl. .................. 73/61 R; 23/230 R; 134/1; 204/1 T
[58] Field of Search .................. 134/1; 210/84; 73/194 EM, 61; 23/230 R, 253; 204/195 P, 1 T

[56] References Cited

U.S. PATENT DOCUMENTS

| | | | |
|---|---|---|---|
| 3,215,272 | 11/1965 | Sweeney | 210/84 |
| 3,229,129 | 1/1966 | Van Haagen | 310/26 |
| 3,360,451 | 12/1967 | Stack | 204/195 P |
| 3,479,873 | 11/1969 | Hermanns | 73/194 EM |
| 3,496,084 | 2/1970 | Stack | 204/195 P |
| 3,664,191 | 5/1972 | Hermanns | 73/194 EM |
| 3,718,567 | 2/1973 | Haddad et al. | 204/195 P |
| 3,771,361 | 11/1973 | Reznick | 73/194 EM |

OTHER PUBLICATIONS

Bauer; "Centri-Cleaner Liquid Cyclones," Bulletin G-33B; 4-71.

*Primary Examiner*—Bradley R. Garris
*Attorney, Agent, or Firm*—Samuel Lebowitz

[57] ABSTRACT

A method for cleaning the sensing probes in a water quality momitoring apparatus, when the probes become coated with a build-up of slime, algae or particulate matter, which comprises the steps of continuously removing particulate matter from the body of the liquid, moving a part of the body of liquid into a confined zone surrounding the probe and applying ultrasonic energy to the confined liquid to remove deposits of foreign matter from the surface of the probe and the liquid confining surface areas.

2 Claims, 1 Drawing Figure

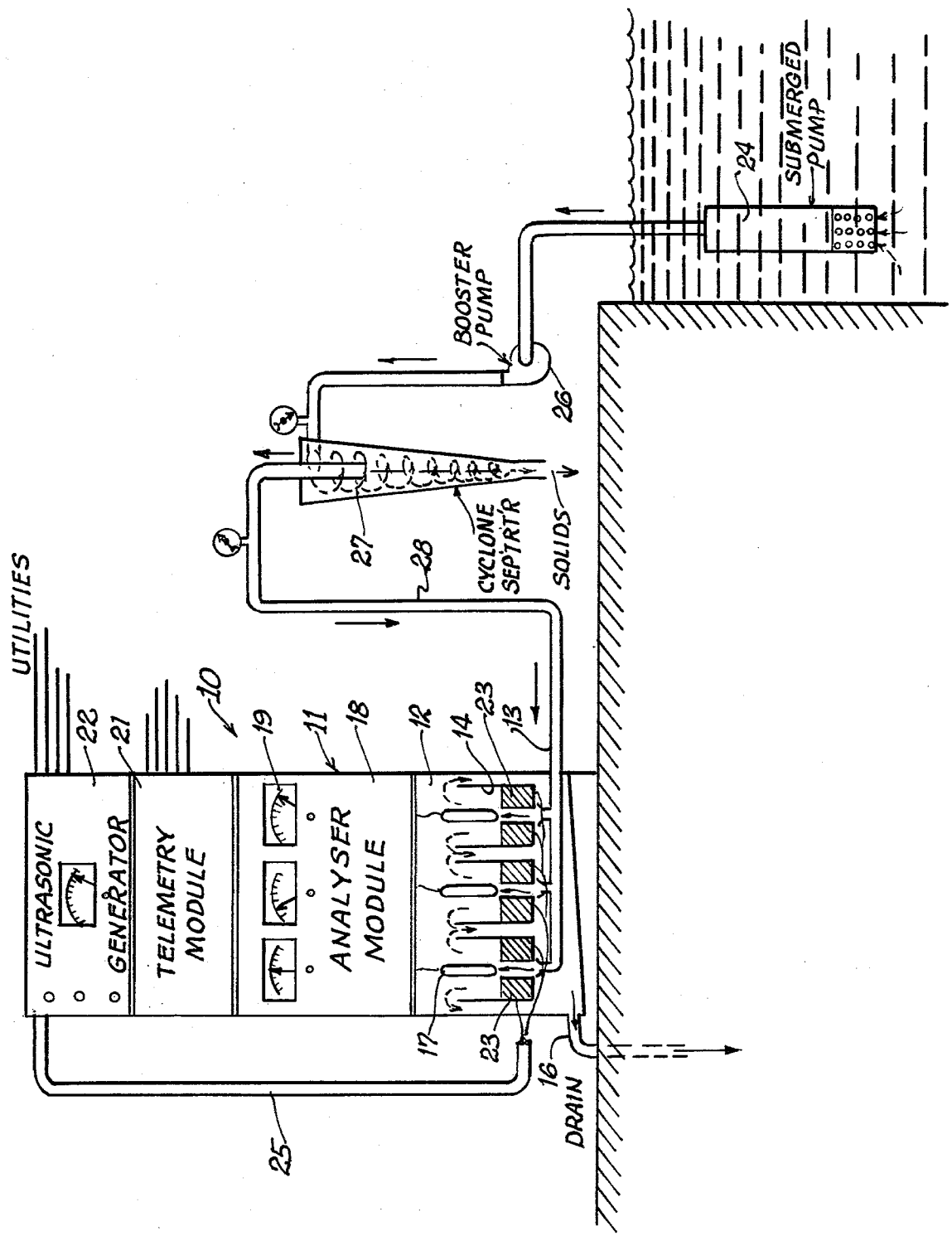

AUTOMATIC CLEANING OF SENSING PROBES

This a continuation of application Ser. No. 479,351, filed June 14, 1974, now abandoned.

BACKGROUND OF THE INVENTION

The current public interest in pollution control has created the need for surveillance and monitoring of environmental conditions particularly related to plant effluent, waterways, sewers, lakes and rivers. The acquisition of accurate and reliable data regarding water quality as affected by industrial wastes, treatment plant effluent, meterological and other factors is necessary for effecting enforcement of standards for pollution control, as well as for analysis and planning.

Automated water quality monitoring systems include monitors at field stations connected by telemetry to a central control data receiving station and rely on the use of automatic unattended measurement procedures operated on a continuous basis, or intermittently, at a predetermined frequency. Sophisticated instrumentation for automatically analyzing physical and chemical parameters, such as pH, conductivity, temperature, dissolved oxygen, chlorides and turbidity of plant effluent and waterways have been utilized in the art. It is recognized that instrument reliability is adversely affected by the fouling of the sampling system or malfunction of the analyzer components that are continously exposed to polluted water. Heavy build-up of slime, algae or particulate matter on the sensing probes, which may comprise solid state or liquid membrane electrodes, and on the surface areas confining the water surrounding the probes, with resulting stagnation of flow deleteriously affects the sensitivity of the probes resulting in inaccurate measurements or measurement failure.

In order to obtain reliable data it has been found necessary to clean the sensing probes manually at frequent periodic intervals, preferably, at least daily. Monitoring stations which are remotely located at substantial distances from a central receiving station must be visited daily by service personnel to effect manual cleaning of the probes and associated apparatus. This requires extensive travel, as well as a substantial expenditure of labor by the service personnel, and represents a significant cost in the maintenance of monitoring stations in the system under consideration. It also has been found that manual removal or displacement of the sensing probes from the monitoring apparatus for manual cleaning disturbs the stability of the calibration resulting in unreliable data.

SUMMARY OF THE INVENTION

The present invention relates to a method utilizing ultrasonic energy in combination with centrifuge means for automatically cleaning the sensing probes and associated apparatus of water quality monitoring apparatus so as to maintain the same in clean condition for maximum sensitivity and reliability, in order to obtain accurate data for effective enforcement of environmental pollution control standards.

The use of ultrasonic electrode cleaning apparatus is known. Typical of such apparatus is the EIL Ultrasonic Electrode Cleaner, Model U 28, manufactured by Cambridge Instrument Co., Inc. of Great Britain.

The use of centrifuge apparatus for removing settleable solids or particulate matter from liquids is known. Typical of such apparatus is the Bauer Centri-Cleaner Liquid Cyclone No. 600-3 manufactured by Bauer Brothers Co., of Springfield, Ohio. Another is the Vulcan Hydro-Clone V 20, manufactured by Vulcan Laboratories, Inc. of Pontiac, Mich.

Insofar as is known to me ultrasonic energy and centrifuge action have never been used, in combination, for cleaning the sensing probes and associated apparatus of water quality monitoring systems. I have found that the use of a centrifuge for removing particulate matter or settleable solids, such as sand, grit, stones etc., from the effluent or water to be tested, before it contacts the sensing probes, reduces the likelihood of injury to the sensing probes and also results in a very marked reduction in over-all build-up of objectionable materials on the surfaces of the probes and associated apparatus, so that subsequent cleaning of the probes and associated apparatus by ultrasonic energy is highly efficient.

The removal of particulate matter or settleable solids from the water before the water contacts the sensing probes is highly desirable in all monitoring situations involving the use of sensing probes, and particularly, in situations involving the use of glass electrodes for pH measurements and liquid membrane electrodes for measuring dissolved oxygen. Particulate matter has abrasive characteristics and would tend to erode the electrodes. In the case of liquid membrane electrodes, the use of very thin Teflon membranes is desirable for obtaining maximum sensitivity to dissolved oxygen changes. Such membranes are fragile and would be subject to excessive degradation if required to withstand the quantity of ultrasonic energy necessary by itself for cleaning the probes of normal build-up of algae, slime etc., and also settleable material incorporated in the build-up. Obviously, in such cases thicker and less sensitive membranes would need to be used to withstand the rigors of such ultrasonic energy for long periods. By reason of the use of a centrifuge, the settleable material is removed before it has an opportunity to contact the membranes and, as a result, the sensing probes require shorter intervals of the application of ultrasonic energy to effect cleansing of the probes. This allows the use of thinner membranes with greater sensitivity of measurement. In a series of comparative tests conducted over a period of several months it was found with the utilization of conventional cleaning practices, with resultant clogging in the sensing zones, that the deviation of measurements from the true value ranged from 1 to 2 parts per million. With the use of my invention the deviation was reduced to 0.22 parts per million, a figure which is within the tolerance of 0.25 parts per million established for an accurate system. In the case of stagnant flow, without cleaning, the deviation could be as high as 10 parts per million.

BRIEF DESCRIPTION OF THE DRAWING

The drawing is a schematic representation of a specific embodiment of my invention.

BRIEF DESCRIPTION OF A PREFERRED EMBODIMENT

Referring to the drawing, there is diagrammatically shown a field station 10 which includes functional components such as an automatic monitor 11 and utilities, all conventional and well known in the art.

Each monitor 11 comprises a flow chamber module 12 which includes an influent pipe 13, a plurality of stainless steel sensor cones or funnels 14, preferably six in number, an overflow drain 16 and individual sensor probes 17 inserted in respective funnels 14 and having associated leads and plugs, not shown. Each monitor 11 also includes an analyzer module 18 in which the electronic signals from the sensor probes 17 are converted to a linear output, amplified to the necessary output voltage and displayed on indicating meters 19. The monitor 11 also includes a telemetry module 21 connected to the central receiving station or control center, not shown. The utilities include electric and telephone services and the necessary pumps and piping. The central station receives data from each monitoring station at periodic intervals in accordance with a predetermined program.

The foregoing components are conventional and from no part of the present invention.

In accordance with my invention I provide each monitor 11 with a fourth module constituting an ultrasonic generator 22 connected by cables 25 to transducers 23 associated with each of the funnels 14 in the flow chamber module 12. This module includes timing apparatus for controlling the operation of the ultrasonic generator 22. The generator may comprise any well known type, for example, Model U28, EIL Ultrasonic Electrode Cleaner manufactured by Cambridge Instrument Company, Inc., and the transducer funnels 14, 23 may comprise either the flow type or dip types, examples of which are Models EIL No. 47 2843 300 and EIL No. 47 2843 400, respectively, both also manufactured by Cambridge Instrument Company, Inc. of Great Britain.

Desirably, the ultrasonic generator 22 should have the capability of operating a multiple number of transducers 23 sequentially with a power output of approximately 100 watts and a frequency output of approximately 80.0 kilohertz. The timing apparatus, not shown, associated with the generator 22 includes two timers, the first, for sequentially applying a manually pre-set interval of ultrasonic power to each transducer 23 for the total cleaning cycle of the multiple sensing probes and the second, for starting and stopping the cleaning cycle and energizing and de-energizing an associate relay, not shown, which functions to transmit a signal to the central receiving station, indicating that the ultrasonic cleaning is in process. This signal is employed in the data acquisition apparatus to notify the central station that the data being transmitted by the monitor 11 to the receiving station during the ultrasonic cleaning interval is unreliable and should be rejected by the data processing equipment.

The delivery of water to the flow chamber 12 from a stream, waterway or plant effluent being monitored is effected by any suitable pump means, if the required pressure is not available. The pump may be of the displacement or submersible type, or both, if the conditions require. For illustrative purposes the drawing shows a submersible pump 24 connected in series with a secondary or booster pump 26, the latter being connected to the inlet of a centrifuge 27 of any suitable type, for example, a Hydro-Clone separator, Model No. V50, manufactured by Vulcan Laboratories, Inc. of Pontiac, Mich. or a Bauer Centri-Cleaner Liquid Cyclone, manufactured by the Bauer Borthers of Springfield, Ohio.

In the centrifuge 27 the solids and particulate matter accumulate in a bottom reservoir for easy separation and disposal and the clean liquid discharged from the centrifuge is conducted by conduit 28 to the transducer funnels 14, 23 in the flow chamber 12. The liquid in each funnel 14 completely surrounds a probe 17 associated therewith. The centrifuge 27 operates continuously to remove particulate matter from the water so that all of the water coming in contact with the sensing probes 17 and the surfaces of the funnels is free of such matter. This not only reduces the likelihood of erosion of the sensing probes 17 but also reduces clogging and stagnation of flow in the funnels 14 and results in a very marked reduction in overall build-up of any objectionable materials on the sensing probes 17 and on the surfaces of the funnels 14. Thus, whatever build-up may occur is more effectively removed by the ultrasonic energy to which the probes 17 and funnel surfaces are subjected during the cleaning cycles. It will be understood that a modified form of apparatus may comprise a plurality of sensing probes associated with a single transducer funnel of sufficient size to encompass the plurality of probes. In such case the probes would be cleaned simultaneously and not sequentially.

The cleaning intervals in which the sensing probes 17 are subjected to ultrasonic energy may be varied depending upon the types and characters of the probes being cleaned. I have found, for example, in most cases, that subjecting an individual probe to ultrasonic energy for an interval of 5–10 minutes, in a 24 hour period is adequate to cleanse the probe and the funnel to maintain the same in clean condition for maximum sensitivity and accuracy. The application of ultrasonic energy for longer intervals would tend to degrade the probe. The timing apparatus in each generator module 22 automatically programs the sequential application of ultrasonic energy to the probes 17 in each flow module 12. After the cleaning intervals, the data transmitted to the central receiving station has sustained accuracy and reliablity.

The automatic cleaning of the sensing probes 17 with minimum disturbance, in accordance with my invention, very materially reduces the frequency of service required to maintain the probes and funnels at optimum operating conditions. Thus, the intervals between visits by service personnel for manual examination, cleaning and calibration of the probes may be extended to once in every three to four week period, instead of daily visits, as in current practices. Also, the use of prior art devices and procedures for cleansing the probes which included the use of filters, dilution methods, periodic chemical cleaning, jet water spray and mechanical wipes are eliminated through the use of my invention.

It will be understood that apparatus for obtaining a composite sample of water for laboratory analysis or turbidity measurement by a turbidimeter may be installed upstream of the centrifuge 27.

Various changes coming within the spirit of my invention may suggest themselves to those skilled in the art; hence, I do not wish to be limited to the specific embodiments shown and described or uses mentioned, but intend the same to be merely exemplary, the scope of my invention being limited only by the appended claims.

I claim:

1. In a fully automated monitoring system of the qualitative conditions of liquids in a body of water subject to environmental changes, which includes the telemetric transmission of the analytic results from a plurality of remotely distributed unmanned treating and field stations to a central data-collecting station with data acquisition apparatus, the method of enhancing the reliability of the analysed and transmitted test results which comprises (a) continuously withdrawing a sample portion of the body of water and continuously centrifuging the sample portion in a closed vessel under pressure to separate the liquid portion from the particulate matter in the water, which separates from the latter and discharges from said vessel, (b) passing the clarified liquid portion to the unmanned station provided with a plurality of membrane-type sensing probes immersed in the liquid portion deposited in container means therefor, for determination of the specific characteristic being analyzed by the appurtenant sensing probe, and (c) applying ultrasonic energy to said sensing probes and container means for a period of approximately five to ten minutes during a period of one day to maintain the sensing probes in clean condition without human intervention.

2. The method set forth in claim 1, including the step of signalling at the time of application of the ultrasonic energy, to indicate the time of such application, and the consequent unreliablity of the qualitative determination of the analysis at this period, for entry into the data acquisition apparatus.

* * * * *